(12) United States Patent
Bertini et al.

(10) Patent No.: US 6,881,755 B2
(45) Date of Patent: Apr. 19, 2005

(54) N-(2-ARYL-PROPIONYL)-SULFONAMIDES AND PHARMACEUTICAL PREPARATIONS CONTAINING THEM

(75) Inventors: Riccardo Bertini, L'Aquila (IT); Cinzia Bizzarri, L'Aquila (IT); Vilma Sabbatini, L'Aquila (IT); Gianfranco Caselli, L'Aquila (IT); Marcello Allegretti, L'Aquila (IT); Maria Candida Cesta, L'Aquila (IT); Carmelo Gandolfi, L'Aquila (IT); Marco Mantovanini, L'Aquila (IT); Francesco Colotta, L'Aquila (IT); Stefano Porzio, L'Aquila (IT)

(73) Assignee: Dompé S.p.A., L'Aquila (IT)

( * ) Notice: Subject to any disclaimer, the term of this patent is extended or adjusted under 35 U.S.C. 154(b) by 56 days.

(21) Appl. No.: 10/460,203

(22) Filed: Jun. 13, 2003

(65) Prior Publication Data

US 2003/0216392 A1 Nov. 20, 2003

Related U.S. Application Data

(62) Division of application No. 09/830,075, filed as application No. PCT/EP99/07740 on Oct. 14, 1999.

(30) Foreign Application Priority Data

Oct. 23, 1998 (IT) .......................... MI98A2280

(51) Int. Cl.$^7$ .............................. A01N 37/18
(52) U.S. Cl. ...................... 514/617; 564/182
(58) Field of Search ................ 514/617; 564/182

(56) References Cited

U.S. PATENT DOCUMENTS

| | | | |
|---|---|---|---|
| 4,082,707 A | 4/1978 | Orzalesi et al. | 260/500.5 H |
| 5,006,542 A | 4/1991 | Hall et al. | 514/381 |
| 5,633,287 A | 5/1997 | Lee et al. | 514/602 |
| 6,117,909 A | 9/2000 | Krause | 514/602 |
| 6,166,064 A | 12/2000 | Dombroski et al. | 514/452 |

FOREIGN PATENT DOCUMENTS

| | | | |
|---|---|---|---|
| EP | 0849256 A1 | | 6/1998 |
| JP | 53-111030 | * | 9/1978 |

OTHER PUBLICATIONS

Kakeya et al., Tetrahedron Letters, vol. 32, No. 10, pp. 1343–1346 (1991).

Regit, Chemische Berichte, vol. 98, No. 4, pp. 1210–1024 (1965).

Belletire et al., Tetrahedron Letters, vol. 27, No. 2, pp. 131–134 (1986).

* cited by examiner

Primary Examiner—Peter O'Sullivan
(74) Attorney, Agent, or Firm—Birch, Stewart, Kolasch & Birch, LLP (57) ABSTRACT

The compounds of formula 1,

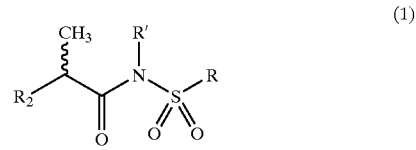

(1)

wherein R and $R_2$ are as defined in the disclosure, are useful in the prevention and treatment of tissue damage due to exacerbated recruitment of polymorphonuclear neutrophils (PMN leukocytes) at the inflammatory sites.

1 Claim, 2 Drawing Sheets

FIGURE 1

FIGURE 2

N-(2-ARYL-PROPIONYL)-SULFONAMIDES AND PHARMACEUTICAL PREPARATIONS CONTAINING THEM

The present invention relates to N-(2-aryl-propionyl)-sulfonamides, and the pharmaceutical preparations thereof useful in the prevention and treatment of tissue damage due to the exacerbate recruitment of polymorphonuclear neutrophils (leukocytes PMN) at the inflammatory sites.

Chemotaxis is a cellular reaction which causes the migration of specific blood cells (macrophages, granulocytes, polymorphonuclear neutrophils), following a chemical stimulus (chemotaxin) towards a concentration gradient of the stimulating agent itself. The most representative chemotaxins are the complement cleavage products C5a, some N-formyl peptides from the lysis of the bacterial surface or of synthetic origin, such as formyl-methionyl-leucyl-phenylalanine (f-MLP) and above all a variety of cytokines ascribable to interleukin IL-8. Interleukin IL-8 is an endogenous chemotactic factor, produced by most nuclear cells (fibroblasts, macrophages, endothelial and epithelial cells) when exposed to TNF-α (Tumor necrosis factor), to interleukins IL-1α and IL-1β and to lipopolysaccharides of the bacterial cell walls (LPS) as well as by neutrophils themselves when they are subjected to the action of LPS and of N-formylpeptides of bacterial origin (fMPL-like peptides). This chemotactic factor [also known as neutrophil activating factor (NAF), T cells chemotactic factor, monocyte-deriving neutrophil chemotactic factor (MDNCF)] controls a series of IL-8 -like chemokines [GROα, β, γ and NAP-2], which bind to the IL-8 receptor (Chang et al., J. Immunol., 148, 451, 1992).

Neutrophils, by action of chemotactic factors, undergo a change of form predisposing them to migration and activation which ends up with degranulation reaction, oxygen consumption and generation of oxygen radicals.

All these events, which take place within a few seconds from the exposure of neutrophils to chemotaxins, are biochemically characterized by a transitory increase in the intracellular levels of $Ca^{2+}$ ions, $Na^+$ ions and c-AMP, with consequent variations in the membrane potential. The increase in $[Ca^{2+}]_i$ induced by chemotaxin is followed by the activation of proteins G, phospholipases C and $A_2$ and of arachidonic acid cascade, with formation of cyclooxygenase and lipooxygenase products (see L. Harvath in Regulation of neutrophil chemotaxis, Ann. Reports in Med. Chem., page 233–235, vol. 24, 1992 and literature cited therein). Neutrophils are the first defense from bacterial infections, due to their aptitude to a rapid migration from peripheral blood through the endothelial junctions and the tissue matrices to the sites where they exert their specific action, i.e. destroying microorganisms, removing damaged cells and stimulating tissue repair (M. A. Goucerot-Podicalo et al., Pathol. Biol. (Paris), 44, 36, 1996).

Under specific pathological conditions, characterized by an exacerbated recruitment of neutrophils, the per se beneficial recruitment action is counteracted by the worsening of the tissue damage, which slows down the healing process and leads, in the most serious cases, to the patient' death.

More recently, a remarkable, convincing evidence supported the hypothesis that ischemia and reperfusion damages and hyperoxia pulmonary damage are related to the presence of activated neutrophils and that cell damage is a direct consequence of this activation. This is proved by experimental models [N. Sekido et al., Nature, 365, 654, 1993 and T. Matsumoto et al., Lab. Investig., 77, 119, 1997] and clinical-pathological reports in humans [A. Mazzone et al., Recent Prog. Med., 85, 397, 1994; T. C. Fisher and H. J. Meiselmann, Thromb. Res., 74 (Suppl. 1), S21–S34, 1994; G. Ricevuti et al., Atheroscl., 91, 1, 1991] according to which cell damages would be directly and strictly related with the extent and the extension PMN leukocytes infiltrate, of which IL-8 cytokine is increasingly considered the most specific and potent activator. During the pathogenesis of these conditions, among the various chemotactic factors activating neutrophils such as C5a, PAF, $LTB_4$ which mediate the direct migration of these neutrophils, IL-8 would play an important role also in that its production by mononuclear phagocytes can mediate the migration of other inflammatory cells both by producing ex-novo IL-8 and by inducing its production by nearby non-immune cells [A. P. Metiko et al., J Clin. Invest, 90, 791 (1992)].

In patients affected with acute respiratory insufficiency (ARDS), the exacerbated presence of neutrophils in the aerial spaces and in pulmonary fluids (which characterizes the disease) significantly correlates with the high concentration of cytokine. On the other hand, the concentrations of NAP-1/IL-8, present in pulmonary oedema fluids of these patients, coincide with the optimum concentrations required for inducing chemotaxis of neutrophils (E. J. Miller et al., Am. Rev. Respir. Dis., 146, 437, 1992); finally, a strict relationship between mortality and high concentrations of IL-8 in alveolar fluids apparently exists (A. Kurdowska et al., J. Immunol., 157, 2699, 1996).

In this contest, particularly significant are the results obtained using anti-IL-8 antibodies, capable of neutralizing cytokine effects in a model of acute respiratory insufficiency and endotoxiemia pulmonary damage by intratracheal instillation of heat-inactivated *Streptococcus pyogenes* (OK-432) (K. Yokoi et al., Lab. Invest., 76, 375 1997).

Patients suffering from acute myocardial infarction show, within 22 hours from its onset, a significant increase in serum IL-8 (13–1100 ng/L). This increase would play a paramount role in the development of myocardium damage due to the high stimulating power of cytokine on neutrophils and on the role of the latter in tissue damage (Y. Abe et al., Br. Heart J., 70, 132, 1993), which, in the clinical evolution of an ischemic event, apparently depends more on the reperfusion process than on the ischemia persistence time.

Recently, the treatment with anti-IL-8 antibodies proved to reduce the cerebral oedema and the extension of the damaged area in a reperfusion model after temporary focal ischemia in rabbit brain (T. Matsumoto et al., Lab. Invest., 77, 119, 1997). The significant increase in IL-8 in brain tissue observed in this model evidences that both the local production of IL-8 in the perfused tissues and its presence in the activated neutrophils in vascular walls cause the extent of the tissue damage.

The receptor interaction between neutrophil and chemotactic agent is considered decisive for chemotaxis; IL-8 takes part in it through two different receptors (CXCR1 and CXCR2) present at the surface of human neutrophils and of some T cells (L. Xu et al., J. Leukocyte Biol., 57, 335, 1995). This would be proved by N-(2-hydroxy-4-nitrophenyl)-N'-(2-bromo-phenyl)urea which inhibits selectively the IL-8 bond to the membrane receptor CXCR2 of neutrophils with a $IC_{50}$ 22 nM (J. R. White et al., J. Biol. Chem, 273, 10095, 1998). A consequence is the blockage of chemotaxis of human neutrophils stimulated by IL-8 (1 nM) and GROα (10 nM) with similar $IC_{50}$ values (20 to 60 nM) [but not that of complement C5a—stimulated chemotaxis in the concentration range of 50 to 330 nM], but not the arrest in the same human neutrophils of the mobilization of $Ca^{2+}_i$ induced by IL-8 or by optimum concentrations of $LTB_4$.

The use of phenylureas in the treatment of Interleukin-8 (IL-8)-mediated pathologies was recently claimed in WO 98/07418 (28.02.1998).

During studies directed to evaluate the contribution that the single enantiomers (S) and (R) of ketoprofen give to the antiinflammatory activity of the racemate and their role in cytokines modulation (P. Ghezzi et al., J. Exp. Pharm. Ther., 1998 in press) it has surprisingly been found that salts of the single enantiomers with chiral and non chiral organic bases dose-dependently inhibits the increase in $Ca^{2+}$ ($[Ca^{2+}]_i$) ions intracell concentration induced by IL-8 in PMN leukocytes (Italian patent application n° MI 98A000146 (28.01.1998) in the Applicant's name). One competition study with La (lanthanium) ions proved that the inhibitory effects of these salts to the neutrophil response to IL-8 was neither the consequence of receptor interaction nor of impaired expression of the number of IL-8 receptors, but the result of a selective block of the action of $Ca^{2+}$ cation, to an extent sufficient to prevent the sequence of events typical of neutrophil activation deriving from cytokine: chemotaxis and degranulation of neutrophils (with the release of elastase, catepsine and other enzymes). Moreover, the single enantiomers inhibit the chemotaxis and the increase in $[Ca^{2+}]_i$ induced by C5a and by fMLP, although less effectively.

The main difference between the two enantiomers is the lower potency (by at least 10–100 times) of the enantiomer (R) as CO enzymes inhibitor.

The enantiomer (R) has, therefore, compared with the enantiomer (S), lower inhibition activity on the synthesis of PG which, in their turn, exert an inhibitory and controlling action on the release of cytokines which, like TNF-α, contribute to amplify the size of the pro-inflammatory effects typical of neutrophils. As a consequence, enantiomer (S) is less therapeutically effective in the treatment of neutrophil-dependent pathologies and inflammatory conditions, such as psoriasis, idiopathic pulmonary fibrosis, acute respiratory insufficiency, reperfusion damages and glomerulonephritis.

It has now been found that N-acyl-sulfonamides of 2-aryl-propionic acids are effective inhibitors of chemotaxis and degranulation of neutrophils induced by IL-8. Similar properties were also evidenced for R (2)-[(4-isobutyl)phenyl] propionamide, described by W. H. Pirke and J. Mc Cune, J. Chromatography, 469, 67, 1989). Therefore, the invention also relates to the use thereof in the treatment of neutrophil-dependent pathologies.

More specifically, the present invention relates to novel N-(2-aryl-propionyl)-sulfonamides of general formula (1):

(1)

in which
$R_2$ is an aryl group,
R is a straight or branched $C_1$–$C_{16}$-alkyl, trifluoromethyl, cyclohexyl, o-tolyl, 3-pyridyl, 2-pyridyl-ethyl, p-cyano-phenylmethyl, p-aminophenylmethyl, 3-cyano-1-propyl, 4-aminobutyl group, an alkoxyethylene $CH_3$—$(CH_2)_{ni}$—$(OCH_2CH_2)_{mi}$-group in which $n_i$ is zero or 1 and $m_i$ is an integer 1 to 3, or a $P_1P_2N$—$CH_2$—$CH_2$— group in which $P_1$ and $P_2$ are independently H, $C_1$–$C_3$-alkyl, benzyloxy-carbonyl, α-, β- or γ-pyridocarbonyl, carboxycarbonyl or carbalkoxycarbonyl, or $P_1$ and $P_2$, when joined to the N atom which they are linked to, form a phthalimido, piperidino, morpholino residue;
R' is H or straight or branched $C_1$–$C_3$-alkyl, preferably hydrogen.

"Aryl group" preferably means phenyl optionally substituted with one to three substituents, which are the same or different, selected from halogen atoms, $C_1$–$C_4$-alkyl, $C_1$–$C_4$-alkoxy, hydroxy, $C_1$–$C_7$-acyloxy, cyano, nitro, amino, $C_1$–$C_3$-acylamino, halo $C_1$–$C_3$-alkyl, halo $C_1$–$C_3$-alkoxy, benzoyl, or the aryl moiety of known anti-inflammatory 2-arylpropionic acids such as ibuprofen, ketoprofen, naproxen, suprofen, carprofen, pirprofen, fenoprofen.

Preferred aryl residues of 2-arylpropionic acids are:
4-isobutylphenyl, 3-benzoylphenyl, 5-bezoyl-2-acetoxyphenyl, 3-phenoxyphenyl, 5-benzoyl-thien-2-yl, 4-thienoylphenyl, 1-oxo-2-isoindolinyl-phenyl, 3-chloro-4-(2,5-dihydro-1H-pyrrol-1-yl)phenyl, 6-methoxy-β-naphthyl, 5-benzoyl-2-thiophenyl, 1-hydroxyphenyl or a residue of formula in which A is benzyl, benzoyl or benzoy-oxime, 1-hydroxy-1-phenyl-methyl, B is hydrogen, hydroxy, $C_1$–$C_3$- acyloxy or amino.

$R_2$ is preferably an aryl residue of a known antiinflammatory 2-arylpropionic acid as defined above.

Particularly preferred meanings of $R_2$ are 4-(2-methyl-propyl)-phenyl, 3-phenoxy-phenyl, 2-[4-(1-oxo-2-isoindolinyl)phenyl], 5-benzoyl-thien-2-yl, 4-thienoyl-phenyl.

Particularly preferred compounds of the invention of formula (1) are those in which the carbon atom to which the methyl group is attached has configuration R.

The compounds of the invention can be prepared using known methods, such as reaction, in an inert solvent, of equimolecular amounts of an acid of formula (2)

(2)

in which $R_2'$ has the same meanings as $R_2$ or is a group which can be transformed into $R_2$ by removing any protecting groups, with equimolecular amounts of a sulfonamide of formula (3):

(3)

in which R and R' have the meanings described above, in the presence of equimolecular amounts and/or of a slight excess of a condensing agent, for example a carbodiimide (such as dicyclohexylcarbodiimide), a soluble carbodiimide (such as N-(3-dimethyl-amino-propyl)-N'-ethylcarbodiimide hydrochloride) or 1,1'-carbonyldiimidazole and of a counterbase selected from the group consisting of triethylamine, 4-(N,N-dimethylamino)-pyridine, 1,8-diazabicyclo[5.4.0]undec-7-ene, and 1,5-diazabicyclo[4.3.0]non-5-ene.

Alternatively, a likewise effective process consists in reacting a sulfonamide anion of formula (3'):

in which R is as defined above, in an inert solvent, with a suitably reactive form of the acids of formula (2); more particularly, the chlorides of acids of formula (2) are the most preferred reactive forms in the process for the preparation of the chiral N-acylsulfonamides of the invention, without coming up against those partial racemizations which could take place during the reaction of a sulfonyl chloride of formula (4) with the anion of an amide of formula (5):

When $R_2'$ in the compounds obtained according to the procedures described above comprises a benzoyl group, said benzoyl can give rise to a different compound of formula (1) through known oximation reactions or through reduction of the carbonyl to alcohol to hydrocarbon (benzyl) upon absorption of one or two hydrogen equivalents in the presence of a suitable catalyst.

The N-acylsulfonamido group of the compounds of formula (1) is a group sufficiently acid to form addition salts with strong and medium bases, such as L-lysine, L-arginine, tromethamine, or chiral amines such as ephedrine, cinchonine, cinchonidine etc, thus providing the optical resolution of said sulfonamides in their single enantiomers (R) and (S). The various chromatography techniques, optionally on chiral carriers (see for example W. H. Pirkle and J. McCune, cited above), such as TLC or the different kinds of column chromatographies, can be used for the purification and separation of enantiomers and diasteromers, whose optical purity is evaluated using R-(-)-2-[(4'-isobutyl)phenyl]propionamide, as a standard reference.

Alkyl-sulfonic, aryl-sulfonic and heteroarylsulfonic acid chlorides, as well as their amides, are known compounds, commercially available or easy to prepare. Therefore, for example, after transformation of a polyoxyethylene alcohol of formula $CH_3—(CH_2)_{ni}—(OCH_2CH_2)_{mi}—OH$ (in which $n_i$ and $m_i$ have the above defined meanings) into the corresponding tosylates or halides (X=Cl, Br or I), the reaction of the latter with a thiourea excess will give the corresponding isothiouronium salts: $CH_3—(CH_2)_{ni}—(OCH_2CH_2)_{min}—S—(C=NH)—NH_2.HX$ which are directly transformed into the corresponding sulfonyl chlorides: $CH_3—(CH_2)_{ni}—(OCH_2CH_2)_{min}—SO_2Cl$ by chlorination at room temperature, and then into the corresponding sulfonamides (J. M. Sprague and T. B. Johnson, J. Am. Chem. Soc., 59, 1837, 1937).

The 2-alkyl-amino-ethanesulfonamides of formula $P_1P_2—N—CH_2—CH_2—SO_2NH_2$ in which of $P_1$ and $P_2$ are a $C_1$–$C_3$-alkyl or $P_1$ and $P_2$, together with the N atom, form a ring as defined above, are known compounds or can be prepared using known methods. For the synthesis of taurine amides see, for example, Miller et al., J. Am. Chem. Soc., 62, 2099, 1940 and H. McIlwain, J. Chem. Soc., 75, 1941; as a general method for the preparation of 2-dialkyl-aminoethanesulfonamides, A. Le Berre and C. Porte, Bull. Soc. Chim. (France) II-602, 1978 disclose the addition of secondary amines (dimethylamine, piperidine and morpholine) to ethylene-sulfonamide [$CH_2=CH—SO_2NH_2$], which synthesis is described in A. S. Matlack, J. Org. Chem., 23, 729, 1958 and references therein cited.

The sulfonamides of formula (3) and the sulfonyl chlorides of formula (4) are compounds known or they can be prepared using well known methods.

2-Aryl-propionic acids of formula (2) are well-known compounds used as analgesic and antiinflammatory drugs. A number of procedures for the preparation thereof, both a single enantiomers and as racemates, are known. Many effective methods for the optical resolution of racemates have been described. Enantioselective synthesis mainly concern (S) enantiomers of arylpropionic acids, but they can also be modified to obtain (R) enantiomers by suitably selecting the reagents (chiral auxiliaries): see, for example, for the use of alkylarylketones as substrates for α-arylalkanoic acids B. M. Trost and J. H. Rigby, J. Org. Chem., 14, 2936, 1978; for α-arylation of Meldrum acid J. T. Piney and B. A. Rowe, Tetrah. lett., 21, 965, 1980; for the use of tartaric acid as chiral auxiliary G. Castaldi et al., J. Org. Chem., 52, 3018, 1987; for the use of α-hydroxyesters as chiral reagents R. D. Larsen et al., J. Am. Chem. Soc., 111, 7650, 1989 and U.S. Pat. No. 4,940,813 and references cited therein).

More particularly, aryl acids of formula (2) in which $R_2$ is 3-benzoyl-2-hydroxy-phenyl or 3-benzoyl-2-aminophenyl are known compounds; a process for the preparation thereof is described in Italian Patent 1,283,649 (23.04.1998), in the Applicant's name.

Specific examples of the compounds of the invention are:

R(−)-N-2-[(4-Isobutylphenyl)-propionyl]-methanesulfonamide and its L(+)-lysine salt;

R(−)-N-2-[(3-benzoylphenyl)-propionyl]-methanesulfonamide;

R(−)-N-(2-[3-(1__-hydroxy-1__-phenyl)methyl]-propionyl)-methanesulfonamide;

R(−)-N-methyl,N-2-[(4-Isobutylphenyl)-propionyl]-methanesulfonamide;

R(−)-N-[2-(3-benzylphenyl)propionyl]-methanesulfonamide;

(±)N-[2-(5'-benzoyl-2'-acetoxyphenyl)-propionyl]-methanesulfonamide;

R(−)-N-2-[(4-Isobutylphenyl)-propionyl]-2-aminoethylsulfona-mide hydrochloride;

R(−)-N-[2-(4-Isobutyl-phenyl)-propionyl]-2-phthalimidoethanesulfonamide;

R(−)-N-[2-(3-benzoyl-phenyl)-propionyl],N'-carbobenzyloxyta-urine amide;

R(−)-N-[2-(3-phenoxy-phenyl)-propionyl],N'-carbobenzyloxyta-urine amide;

R(−)-N-[2-4-(1-oxo-2-isoindolinyl)phenyl]propionyl],N'-carbobenzyloxy-taurine amide;

N-[2-(5-benzoyl-thien-2-yl)-propionyl]-(2-carbobenzyloxyami-no)-ethanesulfonamide;

N-[-2-(4-thienoyl-phenyl)propionyl]-(2-carbobenzyloxyamino)-ethanesulfonamide;

R(−)-N-[2-(4-Isobutyl-phenyl)-propionyl]-(2-carbobenzyloxy-amino)-ethanesulfonamide;
R(−)-N-[2-(3-benzoyl-phenyl)-propionyl]-(2-amino)-ethanesulfonamide;
R(−)-N-[2-(3-phenoxy-phenyl)-propionyl]-(2-amino)-ethanesulfonamide;
N-[2-(5-benzoyl-thien-2-yl)-propionyl]-(2-amino)-ethanesulfonamide;
N-[2-(4-thienoyl-phenyl)propinyl]-(2-amino)-ethanesulfonamide;
R(−)-N-[2-(4-Isobutyl-phenyl)propinyl]-cyclohexylsulfonamide;
R(−)-N-[2-(4-Isobutyl-phenyl)propionyl]-dodecylsulfonamide;
R(−)-N-[2-(4-Isobutyl-phenyl)propionyl]-p-cyanophenylmethanesulfonamide;
R(−)-N-[2-(4-Isobutyl-phenyl)propionyl]-3-cyano-1-propanesulfonamide;
R(−)-N-[2-(4-Isobutyl-phenyl)propionyl]-2-methoxyethanesulfonamide;
R(−)-N-[2-(4-Isobutyl-phenyl)propionyl]-3,6-dioxa-heptylsulfonamide;
R(−)-N-[2-(4-Isobutyl-phenyl)propionyl]-3,6-dioxa-octylsulfonamide;
R(−)-N-[2-(4-Isobutyl-phenyl)propionyl]-3,6,9-trioxa-decylsulfonamide;
R(−)-N-[2-(4-Isobutyl-phenyl)propionyl]-3,6,9-trioxa-undecysulfonamide;
R(−)-N-[2-(4-Isobutyl-phenyl)propionyl]-2-dimethylaminoethylsulfonamide;
R(−)-N-[2-(4-Isobutyl-phenyl)propionyl]-2-(piperidin-1-yl)ethylsulfonamide;
R(−)-N-[2-(4-Isobutyl-phenyl)propionyl]-2-(morpholin-4-yl)ethylsulfonamide.

The compounds of the invention were studied using PMN cells obtained by sedimentation of heparinized blood from healthy volunteers on dextran; the mononuclear cells were removed by means of Ficoll/Hypaque whereas erythrocytes were removed by treatment with hypotonic solutions. Cell viability of PMN leukocytes was calculated by exclusion with Turk and Trypan Blue, while the percentage of PM-nucleates on the cytocentrifugate was evaluated upon staining with Diff Quinck (W. J. Ming et al., J. Immunol., 138, 1469, 1987).

In each of the "in vitro" tests subsequently described, PMN were incubated with the compounds of the invention for 10 minutes at a temperature of 37° C.

In the chemotaxis tests and in those for evaluating cytosol levels of the $Ca^{2+}$ ion, human recombinant IL-8 (Pepro Tech.) was used as stimulating agent: the freeze-dried protein was dissolved in HBSS (Hank's balanced salts solution) at a concentration of 100 ng/mL and was used after dilution in HBSS to concentrations of 10 ng/mL in the chemotaxis tests and of 25–50 ng/mL in the evaluation of $[Ca^{2+}]_i$ cell modifications.

In the chemotaxis test (according to W. Falket et al., J. Immunol. Methods, 33, 239, 1980) PVP filters of 5 mm porosity and a plexigas microcamera suitable to perform 48 replications were used. The microcamera consists of a plexiglas piece containing 48 wells, each of 25 µL capacity, and is equipped with a cover, in its turn containing 48 pores arranged so that, once the lid has been placed on and screwed to the underneath part, 50 µL capacity top compartments are formed in the microcamera.

Equal concentrations of the tested compounds were placed in the top wells containing the PMN suspension and in the lower ones, which contained the carrier optionally added with IL-8 (or a different stimulating agent).

Figure 1:
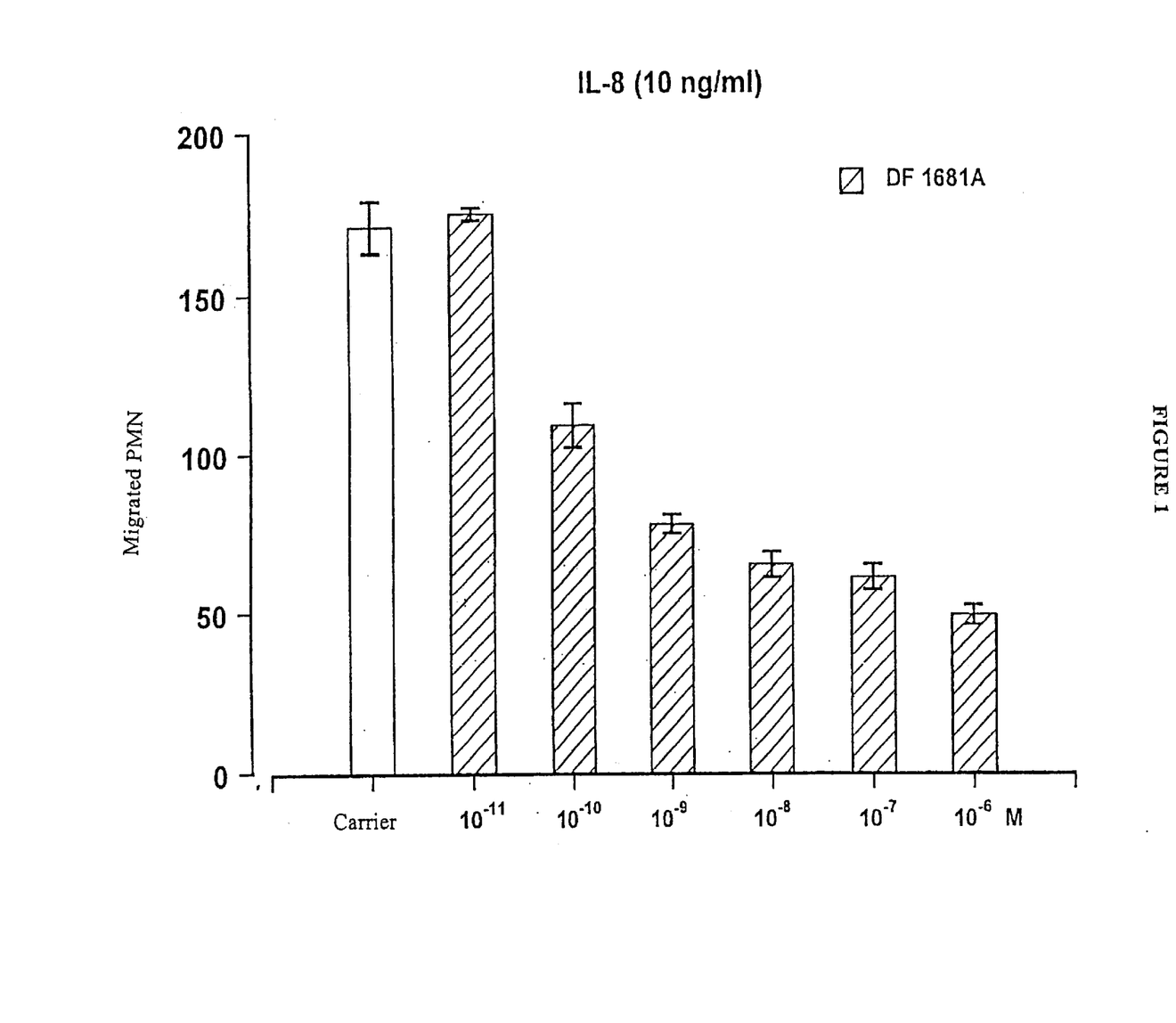

By way of example, R(−)-N-2-[(4-Isobutylphenyl)-propionyl]-methanesulfonamide (DF 1681), dose-dependently inhibits chemotaxis induced by IL-8 (10 ng/mL), in the concentration range from $10^{-6}$ to $10^{-11}$ M. The results, represented as mean±S.D. of 3 independent tests, expressed as number of migrated PMN, are reported in FIG. 1 as histograms.

(S)(+)-N-2-[(4-Isobutylphenyl)-propionyl]-methanesulfonamide and the R(−)-N-2-[(4-Isobutylphenyl)-propionyl]-methanesulfonamide had $IC_{50}$s ranging from $10^{-7}$ to $10^{-8}$ M.

Figure 2:
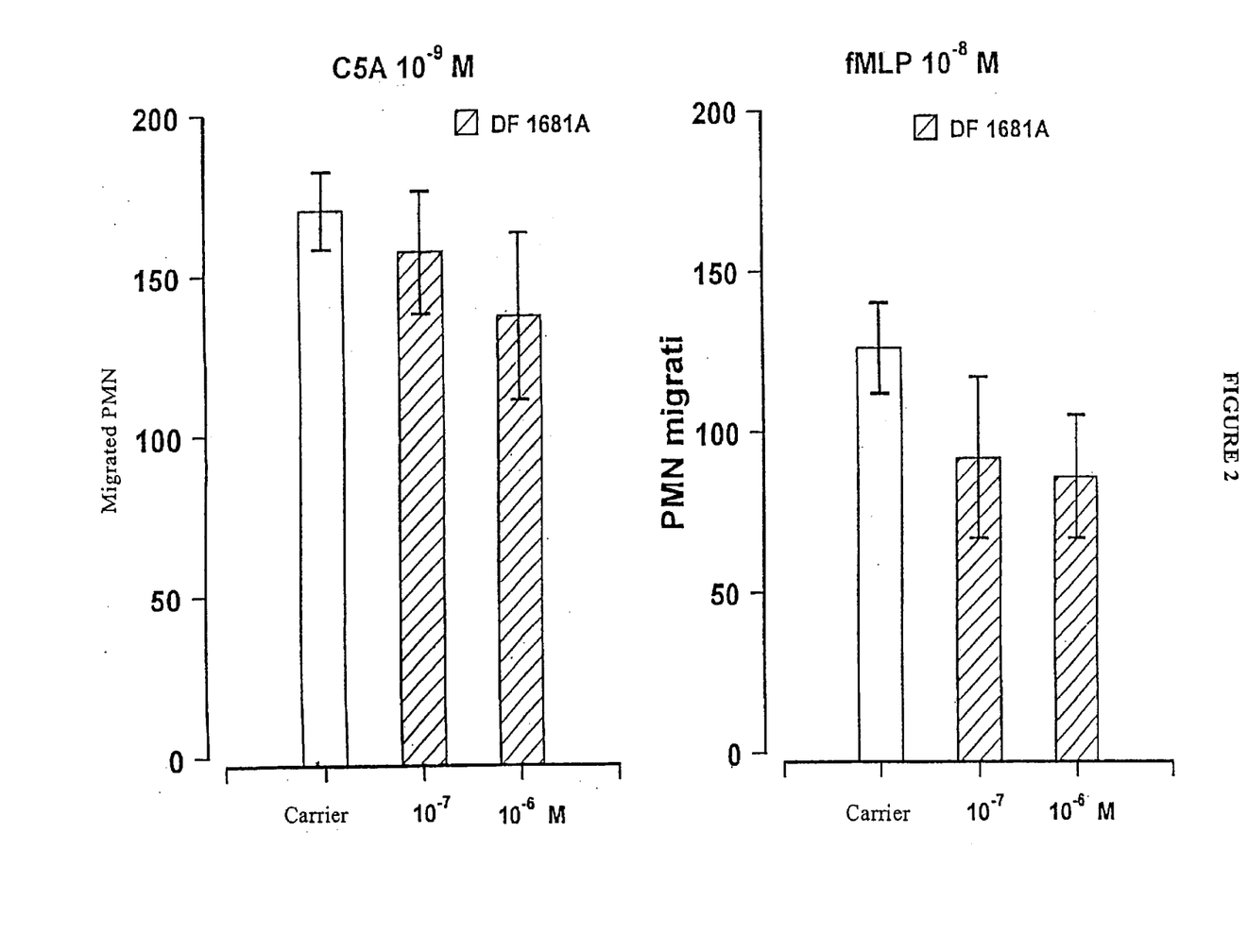

The results reported in FIG. 2 confirm that the compounds of the invention selectivity inhibit IL-8-induced chemotaxis instead of chemotaxis induced by C5a ($10^{-9}$ M) or by f-MLP ($10^{-8}$ M), at least for concentrations ranges of DF 1681 from $10^{-6}$ to $10^{-7}$ M [results, mean+S.D. of 3 independent tests, are expressed as number of migrated PMN].

Cytosol variations of $[Ca^{2+}]_i$ were determined according to the experimental model described by C. Bizzarri et al., (Blood, 86, 2388, 1995), using slides containing adhered PMN added with 1 µM Fura-2AM to evaluate $[Ca^{2+}]_i$ variations in actual time. In their turn, PMN cytocentrifugates were resuspended in RPMI 1640 medium with 5% FCS (bovine foetal serum) at a concentration of $3 \times 10^6$/mL and then inoculated (plated) on round glass slides of 25 mm diameter which were placed in incubator for 30 min. at 37° C. After three subsequent washings with BSS (Balanced salts solution) to remove the non adherent cells, all of the adherent cells were further incubated for a maximum of 4 hours before adding Fura-2AM.

By way of example, results obtained with R(−)-N-2-[3-(benzoylphenyl)-propionyl])-methanesulfonamide (DF 1661) and R(−)-N-2-[(4-Isobutylphenyl)-propionyl]-methanesulfonamide (DF 1681) using human PMNs leukocytes from 3 different donors are reported in the subsequent table. These leukocytes were considered responsive to IL-8 (50 ng/mL) when $[Ca^{2+}]_i$ was higher than the basal value by 34% (normalized at 100) in response to the stimulus.

TABLE

| | |
|---|---|
| IL-8 (50 NG/ML) | 254 ± 23 (n = 20) |
| DF 1661 ($10^{-6}$ M) + IL-8 (50 NG/ML) | 184 + 16 (n = 10) |
| DF 1681 ($10^{-6}$ M) + IL-8 (50 NG/ML) | 159 + 16 (n = 10) |

The responses, expressed as % compared with $[Ca^{2+}]_i$ basal values, are the mean of the values of the responsive cells and include standard error (SEM); n is the number of replications. During these tests, the percentage of non-responsive cells was different in the different groups: 30% in the group treated with only IL-8, 40% in the group pretreated with DF 1661 and 70% in the group pretreated with DF 1681.

The N-2-aryl-propionyl-sulfonamides of the invention of formula (1) are characterized by the capability of inhibiting "in vitro" the chemotaxis of PMN human leukocytes stimulated by interleukin 8. The acylsulfonamides of the invention dose-dependently inhibit the chemotaxis of PMN human leukocytes, with $IC_{50}$s (dose inhibiting the effect by 50%) in the concentration range from $10^{-7}$ to $10^{-9}$ M with a remarkable degree of selectivity and specificity to IL-8-induced chemotaxis. Concentrations higher by one or two magnitudes are necessary to inhibit "in vitro" chemotaxis induced by other chemotactic factors: C5a, formylpeptides of bacterial or synthetic origin (f-LMP). The specificity of the compounds of the invention is proved in that they are capable of inhibiting the increase in $[Ca^{2+}]_i$ intracell concentration in human PMN stimulated by IL-8, which increase is associated with the activation of human PMNL [J. H. Liu et al., J. Infect. Dis., 166, 1089 (1992)].

Independently of the absolute conformation of the methyl, the compounds of the invention are free from significant effects on CO and on PG production. In fact, in LPS-stimulated murine macrophages (1 mg/mL) the compounds of the invention (evaluated in the concentration range from $10^{-5}$ to $10^{-7}$ M) show an inhibition of $PGE_2$ production, often lower than that statistically significant, and never higher than 10–15% of the basal value.

This irrelevant inhibition of $PGE_2$ synthesis is advantageous as the compounds of the invention, contrary to some 2-aryl-propionic acids, in the case of murine macrophages (LPS-stimulated) are not a suitable stimulus for amplifying TNFα synthesis, which in its turn contribute to amplify the neutrophils activation and chemotaxis and Il-8 synthesis. These effects (non amplification of TNF-α synthesis) are also exerted in the case of TNFα synthesis stimulated by hydrogen peroxide.

In consideration of this experimental evidence and as interleukin 8 (IL-8) and its congeners are involved in neutrophil infiltration in pathologies such as psoriasis (B. J. Nickoloff et al., Am. J. Pathol., 138, 129, 1991), rheumatoid arthritis (M. Selz et al., J. Clin. Invest. 87, 463, 1991), ulcerative colitis (Y. R. Mahkla et al., Clin. Sci., 82, 273, 1992), acute respiratory insufficiency (ARDS) and idiopathic fibrosis (P. C. Carré et al., J. Clin. Invest,. 88, 1802, 1991 and E. J. Miller et al., Am. Rev. Respir. Dis. above cited), glomerulonephritis (T. Wada et al., J. Exp. Med., 180, 1135, 1994), the compounds of the invention can be used in the treatment of these pathologies.

For these therapeutical purposes, the compounds of the invention are conveniently formulated in pharmaceutical compositions using conventional techniques and excipients such as those described in "Remington's Pharmaceutical Sciences Handbook" Mack Publishing Co., New York, $18^{th}$ Ed., 1990.

The compositions of the invention can be administered intramuscularly, intravenously, as bolus, in dermatological preparations (creams, lotions, sprays and ointments) as well as by the oral route in the form of capsules, tablets, syrups, controlled-release formulations and the like.

The mean daily dosage will depend on various factors such as severity of the disease and conditions of the patient (age, sex and weight). The dose will generally vary from 1 or a few mg to 1500 mg of the compounds daily, optionally subdivided in multiple administrations. Higher dosages can also be administered thanks to the low toxicity of the compounds of the invention, even for long-term treatments.

The following examples further illustrate the invention.

Preparations

The procedure used for the preparation of alkyl-, arylalkyl-, heteroalkyl-sulfonamides and alkoxy-polyoxyethylene-sulfonamides of formula $CH_3-(CH_2)_{ni}-(OCH_2-CH_2)_{mi}-SO_2NH_2$ in which $n_i$ is zero or the integer 1 and $m_i$ is an integer from 1 to 3 follows what described by J. M. Sprague and T. B. Jonson J.A.C.S.,59, 1837, 1937 and by E. Miller et al., ibidem, 62, 2099 (1940).

Thus, for example, 2-ethoxyethylthiourea hydrochloride is obtained by reacting 2-ethoxyethyl chloride with a slight molar excess of thiourea in alcohol under reflux. Upon bubbling $Cl_2$ in a solution of the salt, cooled at about 25° C., an oily yellow mass separates which is dissolved in ethyl ether and dried over sodium sulfate. The solvent is evaporated off to obtain 2-ethoxyethylsulfonyl chloride which is slowly added to an ammonium hydroxide solution to give 2-ethoxy-ethanesulfonamide which is, if desired, crystallized from diluted alcohol or purified by column chromatography. Using the above process, the following compounds are prepared:

2-methoxy-ethanesulfonamide,
2-(2-methoxy-ethoxy)-ethanesulfonamide or 3,6-dioxa-heptylsulfonamide;
(2-ethoxy-ethoxy)-ethanesulfonamide or 3,6-dioxa-octylsulfonamide;
3,6,9-trioxa-decylsulfonamide;
3,6,9-trioxa-undecylsulfonamide.

EXAMPLE 1

General Methods for the Preparation of a N-acylsulfonamide

A) By Reacting a Chloride of an Acid Formula (2) with a Sulfonamide Anion of Formula (3)

R(−)-N-[2-(4-Isobutylphenyl)propionyl]-methanesulfonamide a) preparation of the acid chloride of formula (2): A suspension of R(−)-2-(4-Isobutylphenyl)-propionic acid R-ibuprofen, 4 g, 0.019 mol) in thionyl chloride (7.4 mL) was refluxed for 4 h; then left to cool spontaneously at r.t.. The thionyl chloride excess was evaporated off under vacuum. The last traces of thionyl chloride were removed washing twice the residual mass with a few drops of dry dioxane and evaporating the solvent under vacuum. 4.66 g (0.019 mol) of R(−)-2-(4-Isobutylphenyl)-propionyl chloride were obtained as yellow oil, which was dissolved in a few ml of anhydrous tetrahydrofuran (THF).

b) Preparation of the Sulfonamide Anion

Methanesulfonamide (2.3 g, 0.0243 mol) was added to a suspension of potassium tert-butoxide (2.73 g, 0.0244 mol) in anhydrous THF (28 mL); the mixture was then stirred for 30 min at r.t. After that, the solution of R(−)-2-(4-Isobutyl)-propionyl chloride (4.66 g, 0.019 mol) was added under stirring, keeping the reaction mixture stirred overnight at r.t.

The separated inorganic salts were filtered off, the solvent was evaporated off under vacuum and the oily residue was partitioned between $CH_2Cl_2$ (30 mL) and a monosodium phosphate saturated solution. The organic phase was washed with water (2×10 mL) and the aqueous phases were extracted with $CH_2Cl_2$ (2×10 mL). The combined organic extracts were dried over $Na_2SO_4$ and the solvent was evaporated off, then the solution of the oily residue in anhydrous MeOH (10 mL) was added with two micro-drops of concentrated sulfuric acid, to esterify to methyl ester any traces of untransformed R(−)-2-(4-Isobutylphenyl)propionic acid. The mixture was kept overnight at r.t., the solvant was cautiously evaporated under vacuum, the residue was partitioned between water (10 mL) and methylene chloride (25 mL). The aqueous phases were discarded and the organic phase was extracted with a $NaHCO_3$, saturated solution (2×20 mL). The basic phases were combined, acidified with conc. HCl and extracted with $CH_2Cl_2$ (3×15 mL). After the usual washings to neutrality, the combined organic extracts were dried over $Na_2SO_4$ and the solvent was evaporated off under vacuum to obtain 1.86 g (0.0066 mol) of R(−)-N-[2-(4-Isobutylphenyl)propionyl]-methanesulfonamide: m.p. 103–105° C. (dec.); $[α]_D$=−68 (c=1; $CH_3OH$); $^1$H-NMR (DMSO-$d_6$) δ 7.3 (d, 2H J=8 Hz); 7.09 (d, 2H J=7 Hz); 3.42 (q, 1H, J=8 Hz); 2.8 (s, 3H); 2.45 (d, 2H, J=7 Hz); 1.55 (m, 1H); 1.3 (d, 3H, J=8 Hz); 0.95 (d, 6H, J=7 Hz).

B) By Direct Condensation of an Acid of Formula (2) with a Sulfonamide of Formula (3) in the Presence of a Condensing Agent N,N-dimethylaminopyridine (2.363 g, 0.0194 mol), N-(3-dimethylaminopropyl)-N'-ethylcarbodiimmide hydrochloride (3.721 g, 0.0194 mol) and methanesulfonamide (1.845 g, 0.0194 mol) were added in succession to a solution of R-(−)-ibuprofen (4 g, 0.0194 mol) in anhydrous $CH_2Cl_2$ (30 mL); the mixture was kept under stirring overnight. The solvent was evaported off, the residue was saponified with ethyl acetate (40 mL) and the combined organic phases were washed with water (15 mL) and a 20% citric acid aqueous solution (2×10 mL) and dried over $Na_2SO_4$, then the solvent was evaporated off to obtain 2.2 g (0.0076 mol) of R(−)-N-[2-(4-Isobutylphenyl)propionyl]-methanesulfonamide, as white solid: m.p. 103–105° C. (dec.); $[\alpha]_D=-68°(c=1; CH_3OH)$.

EXAMPLE 2

Following the procedures described in example 1, the following compounds were prepared:

S(+)-N-[2-(4-Isobutylphenyl)propionyl]-methanesulfonamide: m.p. 109–111° C. (dec.); $[\alpha]_D=73°(c=1; CH_3OH)$; $^1$H-NMR (CDCl$_3$) δ 7.65 (bs, 1H, NH); 7.2–7.0 (m, 4H); 3.65 (q, 1H, J=8 Hz); 3.25 (s, 3H); 2.5 (d, 2H, J=7 Hz); 1.85 (m, 1H); 1.5 (d, 3H, J=8 Hz); 0.95 (d, 6H, J=7 Hz).

R(−)-N-[2-(3-benzoylphenyl)-propionyl]-methanesulfonamide: pale yellow oil; $[\alpha]_D=-73°$ (c=1; CH$_3$OH); $^1$H-NMR (CDCl$_3$) δ 8.25 (bs, 1H, NH), 7.80–7.35 (m, 9H), 3.80 (q, J=7 Hz, 1H), 3.21 (s, 3H),1.55 (d, J=7Hz, 3H).

S(+)-N-[2-(3-benzoylphenyl)-propionyl]-methanesulfonamide: pale yellow oil; $[\alpha]_D=+67°$ (c=1; CH$_3$OH); $^1$H-NMR (CDCl$_3$) δ 8.5 (bs, 1H, NH), 7.9–7.45 (m, 9H), 3.75 (q, J=7 Hz, 1H), 3.21 (s, 3H),1.55 (d, J=7 Hz, 3H).

S(+)-N-[2-(2-fluoro-4-biphenylyl)propionyl]-methanesulfonamide: m.p. 130–132° C.; $[\alpha]_D=+44°$ (c=1; CH$_3$OH); $^1$H-NMR (CDCl$_3$) δ 7.8 (bs, 1H, NH); 7.50–7.30 (m, 5H); 7.05–6.90 (m, 3H); 3.65 (q, 1H, J=7 Hz); 3.20 (s, 3H); 1.50 (d, 3H, J=7 Hz).

S(+)-N-[2-(4-Isobutylphenyl)propionyl]methanesulfonamide: m.p. 109–111° C. (dec); $[\alpha]_D=73°$ (c=1;CH$_3$OH); $^1$H-NMR (CDCl$_3$) δ 7.65 (bs, 1H, NH); 7.2–7.0 (m, 4M); 3.65 (q, 1H, J=8 Hz); 3.25 (s, 3H); 2.5 (d, 2H, J=7 Hz); 1.85 (m, 1H); 1.5 (d, 3H, J=8 Hz); 0.95 (d, 6H, J=7 Hz).

EXAMPLE 3

R(−)-N-methyl,N-[2-(4-Isobutylphenyl)propionyl]-methane-sulfonamide

N-acyl-sulfonamides are sufficiently acid substances to give, after reaction with diazoalkanes, N-acyl-N-alkysulfonamides, according to the process described hereinbelow.

A solution of R(−)-N-[2-(4-Isobtutylphenyl)propionyl]-methanesulfonamide (0.3 g, 0.001 mol) in dry ethyl ether cooled on ice bath (T=4° C.) was added drop by drop to a 0.67 N solution of diazomethane in ethyl ether until persistent yellow colour. The diazomethane excess was destroyed by adding the cooled solution with some drops of glacial acetic acid. The solution was left to stand at r.t. and the solvent was evaporated off. The residue was redissolved in toluene and evaporated under vacuum to remove traces of acetic acid. The oily residue was purified on column chromatography (n-hexane/CH$_2$Cl$_2$ 7:3) to obtain R(−)-N-methyl-N-[2-(4-Isobutylphenyl)propionyl]-methanesulfonamide (0.24 g, 0.00076 mol) as colourless oil. $[\alpha]_D=-60°$ (c=1; CH$_3$OH); $^1$H-NMR (CDCl$_3$) δ 7.2–7.09 (m, 4H); 4.15 (q, 1H, J=8 Hz); 3.2 (s, 3H); 2.9 (s, 3H); 2.45 (d, 2H, J=7 Hz); 1.75 (m, 1H); 1.35 (d, 3H, J=8 Hz); 0.95 (d, 6H, J=7 Hz).

The same compound can be prepared following the procedure of the example 1 using equimolecular amounts of N-methyl-methanesulfonamide instead of methanesulfonamide.

EXAMPLE 4

R(−)-N-[2([3-(1S-hydroxy-1S-phenyl)methyl]-phenyl) propionyl]-methanesulfonamide A solution of 0.5 g of N-(R(−)-2-[3-(benzoylphenyl)-propionyl])-methanesulfonamide in ethanol, added with 0.05 ml of triethylamine and a catalytic amount of 5% Pd/C, was kept under H$_2$ atmosphere until absorption of one molar equivalent of gas. The catalyst was filtered off through celite and the eluate was evaporated to dryness. The residue was partitioned between ethyl ether and a 5% NaH$_2$PO$_4$ aqueous solution and the organic phase gave 0.4 g of R(−)-N-[2([3-(1S-hydroxy-1S-phenyl)methyl]-phenyl)-propionyl]-methanesulfonamide.

EXAMPLE 5

R(−)-N-2[3-(benzylphenyl)-propionyl]-methane-sulfonamide

A solution of 0.5 g of N-(R(−)-2-[3-(benzoylphenyl)-propionyl])-methanesulfonamide in ethanol was added with 0.05 ml of triethylamine and a catalytic amount of 5% Pd/C, and kept under H$_2$ atmosphere until absorption of at least two molar equivalents of gas. The catalyst was filtered off through celite and the eluate was evaporated to dryness. The residue was partitioned between ethyl ether and a 5% NaH$_2$PO$_4$ aqueous solution and the organic phase gave 0.4 g of R(−)-N-2[3-(benzylphenyl)-propionyl]-methanesulfonamide.

EXAMPLE 6

(±) N-2-[(5'-Benzoyl-2'-acetoxyphenyl)-propionyl]-methanesulfonamide

A solution of 6 g of (±) 4-acetoxy-3-(1'-methyl-2'-propen-1-yl)-benzophenone in CH$_2$Cl$_2$ (125 mL) added with an equivalent volume of H$_2$O was added in succession under strong stirring with: glacial acetic acid (12 mL, Aliquat 336 (0.37 g) and, in small portions, potassium permanganate for a total 9.5 g (0.060 mol). The mixture was kept under stirring for 20 h at r.t. until complete disappearance of the starting product. The reaction mixture was decolourized by addition of a sodium metabisulfite aqueous solution (7.2 g in H$_2$O, 15 mL), a further CH$_2$Cl$_2$ (10 mL) was added, then phases were separated. The organic phase was washed with brine (2×25 mL) and dried over Na$_2$SO$_4$, the solvent was evaporated off under vacuum to obtain 6.2 g of (±) 2-(5'-benzoyl-2'-acetoxyphenyl)-propionic acid as oily mass, of good purity. HPLC H$_2$O/CH$_3$CN t=0 60 40, t=12 0 100, t=15 0 100. Bondapak C18 20 cm, 1=254 nm r.t.=5.5 min.). TLC (CH$_2$Cl$_2$/CH$_3$OH 9:1) Rf=0.2; $^1$H-NMR (CDCl$_3$) δ 7.95 (s, 1H); 7.85 (dd, 2 H, J'=7 Hz); 7.75 (dd, 1 H, J'=7 Hz); 7.6 (m, 1 H,); 7.45 (7,2 H, J=7 Hz); 7.25 (s, 1H); 3.9 (q, 1H, 8 Hz); 2.35 (s, 3H); 1.5 (d, 3H, J=8 Hz)

Using this compound in the process of example 1, (+)N-2-[(5'-benzoyl-2'-acetoxyphenyl)-propionyl]-methanesulfonamide was obtained.

EXAMPLE 7

R(−)-N-[2-(4-Isobutylphenyl)propionyl]-methanesulfonamide L(±)-lysine salt

A solution of L(+)-lysine (129 mg; 0.88 mmol) in water (1.3 mL) was added to a solution of R(−)-N-[2-(4-

Isobutylphenyl)propionyl]-methanesulfonamide (250 mg; 0.88 mmol) in 1 ml of methanol. The solvent was evaporated off and the residual mass was taken up with ethyl ether (5 mL) and stirred overnight at room temperature. The crystalline, highly hygroscopic material which separated was filtered quickly under nitrogen atmosphere, washed on the filter with anhydrous ethyl ether and dried under vacuum at 50° C. for 2 h to give 360 mg of R(−)-N-[2-(4-Isobutylphenyl)propionyl]-methanesulfonamide salt of L(+)-lysine as pale yellow powder. $[\alpha]_D=-17.3°$ (c=1.15; $CH_3OH$); $^1H$-NMR ($D_2O$): δ 7.30 (dd, 4H, J=8 Hz), 3.77 (t, 1H, J=7 Hz), 3.65 (q, 1H, J=7 Hz), 3.05 (m, 5H), 2.52 (d, 2H, J=7 Hz), 1.92 (m, 2H), 1.75 (m, 2H) 1.50 (m, 3H), 1.40 (d, 3H, J=7 Hz), 0.90 (6H, d, J=7 Hz).

EXAMPLE 8

R(−)-2-[(4'-Isobutyl)phenyl]propionamide

Using in the procedure of example 1 a 28% $NH_4OH$ aqueous solution instead of the sulfonamido anion, according to the process herein described, the amides of the acids of formula (2) were prepared. A solution of 1 g of R(−)-2 [4-Isobutyl-phenyl]-propionyl chloride in dry acetonitrile (1.5 mL) was dropped into a 28% $NH_4OH$ solution (3 mL), cooled to 0°–5° C., at such a rate that the reaction temperature mixture did not exceed +5° C. The mixture was left under stirring for 1 hour at r.t., the solvents were evaporated off under reduced pressure to give a residue which was dissolved in ethyl acetate (5 mL). The solution was cooled to 0°–40° C. to separate a white crystalline precipitate (1.218 g; 5.93 mmol) of R(−)-2-[(4'-isobutyl)phenyl]propionamide which was filtered and dried under vacuum: m.p. 125–127° C.; $[\alpha]_D=-28°$ (c=1; $CH_3OH$); $^1H$-NMR ($CDCl_3$) δ 7.2–7.05 (m, 4H); 5.25 (bs, 2H, N$\underline{H}_2$), 3.6 (q, J=8 Hz, 1H), 2.5 (m, 2H), 1.9 (m, 1H), 1.55 (d, J=8 Hz, 3H), 0.93 (d, J=7 Hz, 6H)

EXAMPLE 9

R(−)N-[2-(4-Isobutylphenyl)propionyl]-(2-amino) ethylsulfonamide hydrochloride

Following the method described by Winterbottom, R. et al., J. Am. Chem. Soc., 69, 1393–1401 (1947), 21.4 g of phthalic anhydride (0.145 mol) were added to a suspension of taurine (17 g, 0.137 mol) and potassium acetate (14.2 g, 0.145 mol) in glacial acetic acid (48 mL), heated under reflux. Heating was continued to obtain the complete dissolution of the reagents (2.5 h); after cooling to 0°–5° C., a precipitate formed which was separated by filtration, washed with glacial acetic acid and absolute ethanol, dried in the air and under vacuum (50° C.), to give 31.2 g of 2-phthalimidoethanesulfonic acid potassium salt [m.p. >300° C.; $^1H$-NMR ($D_2O$) d 7.85 (m, 4H), 4.05 (t, 3H, J=8 Hz), 3.25 (t, 2H, J=8 Hz). A suspension of 5 g of the salt in benzene (50 mL), dried by azeotropical distillation, was added with 2.56 g of phosphorous pentachloride (0.015 mol) and refluxed for 1 h. Then a second aliquot of phosphorous pentachloride (2.56 g, 0.015 mol) was added. The mixture was refluxed for a further 90 min, then solvents and reagents were evaporated off under vacuum and reduced pressure. The mixture was refluxed for a further 1.30 hours; cooled to r.t. and the solvents were evaporated under reduced pressure. The residue was taken up into 30 g of finely triturated ice to form a fine solid (which was filtered, washed with water and dried) of 2-phthalimidoethanesulfonyl chloride (3.71 g; m.p. =158–159° C.).

A 28% ammonia solution (15.5 mL) in acetonitrile (15 mL) was dropped into a solution of 2-phthalimidoethanesulfonyl chloride in acetonitrile (30 mL), cooled to 0°–4° C., the mixture was stirred for 30' at 0–4° C., the solvent was evaporated off and the residual mass was added with hot water to separate a precipitate of 2-phthalimidoethanesulfonamide (0.8 g) [m.p.=206°–209° C.; $^1H$-NMR (DMSO-$d_6$) δ 7.95 (m, 4H), 7.15 (bs, 2H, $NH_2$), 4.05 (t, 3H, J=8 Hz), 3.35 (t, 2H, J=8 Hz)]

0.75 g (0.00295 mol) of the compound were added under inert gas atmosphere to a suspension of potassium tert-butoxide (0.331 g, 0.00295 mol) in anhydrous THF (7 mL); the mixture was stirred for 1 h, then added with a solution of R(−)2-(4-isobutyl-phenyl)-propionyl chloride [freshly prepared starting from 0.47 g of the acid (0.00227 mol) by reaction with thionyl chloride] in anhydrous THF (2 mL). The mixture was kept under stirring at r.t. for 24 h; the solid residue was filtered off, the solution was evaporated to dryness and the residue was partitioned between water and ethyl acetate. The combined organic phases were washed with water (2×25 mL) and brine (25 mL) and dried over $Na_2SO_4$ as usual) was obtained, the solvent was evaporated off under vacuum, to obtain an oily residue which was purified by flash chromatography (eluent $CH_2Cl_2/CH_3OH$ 98:2), to yield a transparent oil, 0,6 g of N-[R(−)2-(4-isobutyl-phenyl)-propionyl]-2-phthalimido-ethanesulfonamide. $^1H$-NMR ($CDCl_3$) δ 8.05 (m, 4H), 7.15 (m, 4H), 7.05 (bs, 1H, N$\underline{H}$), 4.05 (t, 3H, J=8 Hz), 3.35 (m, 3H), 2.50 (d, 2H, J=7 Hz), 1.92 (m, 1H), 1.20 (d, 3H, J=8 Hz), 0.95 (d, 6H, J=7 Hz).

A solution of the compound (0.5 g, 1.12 mmol) in ethanol (4 mL), added with 85% hydrazine hydrate (0.4 mL) was refluxed for 1 hour. After evaporation of the solvent under vacuum, dilution with water and acidification with 2N hydrochloric acid, phthalylhydrazide was separated by filtration. The eluate was evaporated to dryness to give 0.332 g of R(−)-N-[2-(4-Isobutyl-phenyl)-propionyl]-(2-amino) ethane-sulfonamide hydrochloride, also named R(−)N-[2-(4-isobutyl-phenyl)-propionyl] taurinesulfonamide hydrochloride.

EXAMPLE 10

Using in the process of example 9 N'-carbobenzyloxytaurine amide, prepared according to H. McIlwain, J. Chem. Soc., 75, 1941) and a 2-aryl-propionic acid chloride selected from the group consisting of R(−)2-(3-benzoyl-phenyl)-propionic, R(−)2-(3-phenoxy-phenyl)-propionic, R(−)2-[4-(1-oxo-2-isoindolinyl)-phenyl] propionic, 2-(5-benzoyl-thien-2-yl)-propionic, 2-(4-thienoyl-phenyl)-propionic and R(−)-2-(4-isobutyl-phenyl)-propionic, the following compounds were obtained, respectively:

R(−)-N-[2-(3-benzoyl-phenyl)-propionyl]-(2-carbobenzyloxyamino)-ethanesulfonamide;

R(−)-N-[2-(3-phenoxy-phenyl)-propionyl]-(2-carbobenzyloxyamino)-ethanesulfonamide;

R(−)-N-[2-[4-(1-oxo-2-isoindolinyl)-phenyl)-propionyl]-(2-carbobenzyloxyamino)ethanesulfonamide;

N-[2-(5-benzoyl-thien-2-yl)-propionyl]-(2-carbobenzyloxyamino)-ethanesulfonamide;

N-{2-[4(2-thienoyl-phenyl)]propionyl}-(2-carbobenzyloxyamino)ethanesulfonamide;

R(−)-N-2-[4-Isobutyl-phenyl)-propionyl]-(2-carbobenzyloxyamino)-ethanesulfonamide.

EXAMPLE 11

A suspension of 2 g of R(−)-N-[2-(4-Isobutyl-phenyl)-propionyl]-(2-carbobenzyloxy)ethanesulfonamide and 0.1 g of palladium black in a mixture of water (20 mL), methanol (20 mL) and acetic acid (6 mL) was stirred under hydrogen atmosphere; the carbon dioxide evolution stopped in ½ h. The suspension was filtered to remove Pd, the solvent was evaporated under vacuum. The residue was kept under vacuum in the presence of NaOH. A solution of this residue in some ethanol (5 mL) was treated with an HCl saturated solution in ethanol to separate R(–)-N-[2-(4-isobutyl-phenyl)-propionyl]-(2-amino)ethanesulfonamide hydrochloride which was collected by filtration.

Using in the same procedure the carbobenzyloxytaurine-imides of example 10 the following compounds were obtained, as hydrochlorides:
R(–)-N-[2-(3-benzoyl-phenyl)-propionyl]-(2-amino)-ethanesulfonamide;
R(–)-N-[2-(3-phenoxy-phenyl)-propionyl]-(2-amino)-ethanesulfonamide;
R(–)-N-[2-[4-(1-oxo-2-isoindolinyl)-phenyl]-propionyl]-(2-amino)ethanesulfonamide;
N-[2-(5-benzoyl-thien-2-yl)-propionyl]-(2-amino)-ethanesulfonamide;
N-{2-[4(2-thienoyl-phenyl)]propionyl}-(2-amino)-ethanesulfonamide.

EXAMPLE 12

Using in the process of example 1 a sulfonamide selected from the group consisting of cyclohexylsulfonamide, hexyl-, dodecyl- or hexadecylsulfonamide, p-cyanophenylmethanesulfonamide, 3-cyano-1-propanesulfonamide, 2-methoxyethane-sulfonamide, 3,6-dioxa-heptylsulfonamide 3,6-dioxa-octylsulfonamide; 3,6,9-trioxa-decylsulfonamide; 3,6,9-trioxa-undecylsulfonamide, the following compounds were obtained:
R(–)-N-[2-(4-Isobutyl-phenyl)propionyl]-cyclohexyl-sulfona-mide;
R(–)-N-[2-(4-Isobutyl-phenyl)propionyl]-hexyl-sulfonamide;
R(–)-N-[2-(4-Isobutyl-phenyl)propionyl]-dodecyl-sulfonamide;
R(–)-N-[2-(4-Isobutyl-phenyl)propionyl]-hexadecyl-sulfonami-de;
R(–)-N-[2-(4-Isobutyl-phenyl)propionyl]-p-cyano-phenylmethanesulfonamide;
R(–)-N-[2-(4-Isobutyl-phenyl)propionyl]-3-cyano-1-propanesulfonamide;
R(–)-N-[2-(4-Isobutyl-phenyl)propionyl]-2-methoxy-ethanesulfonamide;
R(–)-N-[2-(4-Isobutyl-phenyl)propionyl]-3,6-dioxa-heptylsulfonamide;
R(–)-N-[2-(4-Isobutyl-phenyl)propionyl]-3,6-dioxa-octylsulfonamide;
R(–)-N-[2-(4-Isobutyl-phenyl)propionyl]-3,6,9-trioxa-decylsulfonamide;
R(–)-N-[2-(4-Isobutyl-phenyl)propionyl]-3,6,9-trioxa-undecylsulfonamide.

If desired, when a solution of one of the cyanosulfonamides selected from the group of: R(–)-N-[2-(4-isobutyl-phenyl)propionyl]-p-cyanophenylmethanesulfonamide and R(–)-N-[2-(4-isobutyl-phenyl)propionyl]-3-cyano-1-propanesulfonamide were hydrogenated in ethanol containing gaseous HCl in the presence of platinum oxide, the hydrochlorides of the following sulfonamides were obtained:
R(–)-N-[2-(4-Isobutyl-phenyl)propionyl]-p-amino-methylphenylmethanesulfonamide;
R(–)-N-[2-(4-Isobutyl-phenyl)propionyl]-4-amino-1-butanesulfonamide.

EXAMPLE 13

Using in the process of example 1 a sulfonamide selected from the group consisting of 2-dimethylamino-ethylsulfonamide, 2-(piperidin-1-yl)-ethylsulfonamide and 2-(morpholin-4-yl)-ethylsulfonamide, were obtained:
R(–)-N-[2-(4-Isobutyl-phenyl)propionyl]-2-dimethylamino-ethylsulfonamide;
R(–)-N-[2-(4-Isobutyl-phenyl)propionyl]-2-(piperidin-1-yl)-ethylsulfonamide;
R(–)-N-[2-(4-Isobutyl-phenyl)propionyl]-2-(morpholin-4-yl)-ethylsulfonamide.

EXAMPLE 14

Using in the process of example 1 R(–)-2-(3-benzoyl-phenyl)propionyl chloride and a sulfonamide selected from the group consisting of trifluorimethylsulfonamide, o-tolylsulfonamide, 3-pyridylsulfonamide and 4-pyridyl-ethanesulfonamide, the following compounds were obtained:
R(–)-N-[2-(3-benzoyl-phenyl)propionyl]-trifluoro-methylsulfonamide;
R(–)-N-[2-(3-benzoyl-phenyl)propionyl]-o-tolyl-sulfonamide;
R(–)-N-[2-(3-benzoyl-phenyl)propionyl]-(3-pyridyl)-sulfonamide;
R(–)-N-[2-(3-benzoyl-phenyl)propionyl]-2 (4-pyridyl)-ethanesulfonamide.

EXAMPLE 15

A solution of 0.35 g of R(–)-N-[2-(3-benzoyl-phenyl) propionyl]-trifluoromethylsulfonamide in 5 ml of pyridine was added with 0.11 g of hydroxylamine hydrochloride. The mixture was reacted at room temperature for 12 hours, then the solution was dropped into 40 ml of 2N $H_2SO_4$. The formed precipitate was extracted with ethyl acetate (3×8 mL). The organic phases were combined, washed with water to neutral, dried over sodium sulfate and evaporated to dryness to give 0.36 g of R(–)-(Z,E)-N-[2-(3-benzoyl-phenyl)propionyl]-trifluoromethylsulfonamide oxime.

Using R(–)-N-[2-(3-benzoyl-phenyl)propionyl]-methanesulfonamide in the process described above, R(–)-(Z,E)-N-[2-(3-benzoyl-phenyl)propionyl]-methane-sulfonamide oxime was obtained.

EXAMPLE 16

R(–)2-(4'-isobutyl)phenylpropionyl-(2"-N-nicotinoyl-amino)ethanesulfonamide

A solution of nicotinic acid (0.565 g; 4.6 mmol) in thionyl chloride (3.07 mL; 42.3 mmol) was refluxed for 3 h and cooled at room temperature to give, after drying under vacuum, nicotinoyl chloride as a pale yellow solid (0.65 g). A mixture of the resulting nicotinoyl chloride (0.64 g; 4.52 mmol) in N,N-dimethylformamide (DMF, 1 mL) was added drop by drop to a solution of R(–)2-(4'-isobutyl) phenylpropionyl-(2"-amino)ethanesulfonamide (0.6 g; 1.92 mmol) and triethylamine (1 mL) in DMF (10 mL). The resulting mixture was stirred for 24 h at r.t. DMF was evaporated under vacuum; the crude residue was purified by column chromatography (eluent: $CHCl_3/CH_3OH$/Cyclohexane/$NH_4OH$ 60:14:24:2) to give R(–)2-(4'-isobutyl)phenylpropionyl-(2"-N-nicotinoylamino)-ethanesulfonamide, $[\alpha]_D$=–10.7 (c=0.15; EtOH); as a colourless oil (0.56 g; 1.34 mmol), MW=417.53, MS=m/z 418.5 (ES)1; TLC ($CHCl_3/CH_3OH$/Cyclohexane/$NH_4OH$ 60:14:24:2) Rf=0.4

$^1$H-NMR (CD$_3$OD) δ ppm 9.2–9.0 (bs, 1H, N$\underline{H}$); 8.7–8.5 (bs, 1H, N$\underline{H}$); 8.4 (d, 1H, J=8 Hz); 7.9 (m, 1H); 7.5–7.4 (m, 1H); 7.35 (s, 1H); 7.25 (d, 2H, J=8 Hz); 7.05 (d, 2H, J=8 Hz); 3.8–3.5 (m, 5H); 2.5 (d, 2H, J=7 Hz); 1.95–1.8 (m, 1H); 1.45 (d, 3H, J=7 Hz); 0.9 (d, 6H, J=7 Hz).

Using in the above procedure the isonicotinic and the picolinic acids instead of the nicotinic one the following compounds are obtained:

R(−)2-(4'-isobutyl)phenylpropionyl-(2"-N-isonicotinoylamino)ethanesulfonamide;

R(−)2-(4'-isobutyl)phenylpropionyl-(2"-N-picolinoylamino)ethanesulfonamide.

EXAMPLE 17

R(−)2-(4'-isobutyl)-phenylpropionyl-(2"-N-carboxycarbonylamino)ethanesulfonamide A solution of ethyl chlorooxoacetate (0.62 g; 4.52 mmol) in DMF (1 mL) was added drop by drop to a stirred solution of R(−)2-(4'-isobutyl)phenylpropionyl-(2"-amino)ethane sulfonamide (0.6 g; 1.92 mmol) and triethylamine (1 mL) in DMF (10 mL). The resulting mixture was stirred for 24 h at r.t. The DMF was evaporated off under vacuum; the crude residue was diluted with water and extracted with diethyl ether (3×10 mL). The collected organic extracts were washed with water (2×15 mL) and brine (20 mL), dried over Na$_2$SO$_4$ and evaporated under vacuum to give R(−)2-(4'-isobutyl)phenylpropionyl-(2"-N-ethyloxalylamino)-ethanesulfonamide as a colourless oil (0.51 g; 1.25 mmol).

A solution of the above R(−)2-(4'-isobutyl)-phenylpropionyl-(2"-N-ethyloxalylamino)ethane sulfonamide (0.5 g; 1.22 mmol) in dioxane (1.55 mL) was added with 1N NaOH (1.55 mL) and stirred overnight at r.t. Dioxane was removed under vacuum, then the aqueous residue was diluted with water; 4N H$_2$SO$_4$ was added to pH=2; the aqueous phase was extracted with dichloromethane (4×15 mL); the collected organic extracts were washed with water (2×15 mL) and brine (15 mL), dried over Na$_2$SO$_4$ and evaporated under vacuum to give R(−)2-(4'-isobutyl)-phenylpropionyl-(2"-N-carboxycarbonylamino) ethanesulfonamide as colourless oil (0.426 g; 1.1 mmol); TLC (CHCl$_3$/CH$_3$OH/H$_2$O 65:25:4) Rf=0.5; [α]$_D$=−60 (c=1; CH$_3$OH);

$^1$H-NMR (CD$_3$OD) δ ppm 10.55–10.0 (bs, 1H, COO$\underline{H}$); 7.25 (d, 2H, J=8 Hz); 7.05 (d, 2H, J=8 Hz); 3.8–3.5 (m, 5H); 2.5 (d, 2H, J=7 Hz); 1.95–1.8 (m, 1H); 1.45 (d, 3H, J=7 Hz); 0.9 (d, 6H, J=7 Hz).

EXAMPLE 18

R(−)2-(4'-isobutyl)-phenylpropionyl-(2"-N-benzyloxycarbonylamino)ethanesulfonamide Taurine (1 g; 8 mmol) was dissolved in 2N NaOH (4.3 mL) and, after cooling on ice/water bath, 4N NaOH (2.14 mL) and a solution of benzyloxycarbonyl chloride (3.27 mL; 8 mmol) in toluene (3 mL) were dropped at same time. After the additions, the mixture was left stirring at T=0–5° C. for 1 h. The reaction was quenched by adding diethyl ether. The mixture was debated and the phases were separated. The aqueous one was cooled to 0–5° C. and 37% HCl was added to pH=2. The acidic phase was extracted with ethyl acetate (3×10 mL) and the collected organic extracts were washed with water (2×15 mL) and brine (15 mL), dried over Na$_2$SO$_4$ and evaporated under vacuum to give 2-(N-benzyloxycarbonylamino)ethanesulfonic acid as crude product purified by trituration in diethyl ether to give the pure product as white solid (1.46 g; 5.64 mmol Yield= 70.5%)

2-(N-benzyloxycarbonylamino)ethanesulfonic acid (0.6 g; 2.31 mmol) was suspended in dry toluene (6 mL) and PCl$_5$ was added (0.65 g; 3.11 mmol). The mixture was refluxed for 2 h, until complete dissolution of the reagents. After cooling at room temperature, the solvent was evaporated off under vacuum to give the crude 2-(N-benzyloxycarbonylamino)-ethanesulfonyl chloride pure enough for the next step.

Crude 2-(N-benzyloxycarbonylamino)ethanesulfonyl chloride was dissolved in acetonitrile (10 mL). The resulting solution was cooled on an ice/water bath and a solution 1:1 of 28% NH$_4$OH (5 mL) and acetonitrile (5 mL) was dropped therein. After stirring for 30', the solvents were evaporated off under vacuum and the crude residue was recrystallised with methanol to give 2-(N-benzyloxycarbonylamino) ethanesulfonamide as white powder (0.51 g; 1.96 mmol).

R(−) Ibuprofen (0.32 g; 1.55 mmol) was dissolved in dry dichloromethane (7.5 mL) and added with N,N-dimethylaminopyridine (0.19 g; 1.55 mmol) and dicyclohexylcarbodiimide (0.32 g; 1.7 mmol); the resulting mixture was left stirring for 30'. Then 2-(N-benzyloxycarbonylamino)ethanesulfonamide (0.4 g; 1.55 mmol) was added and the mixture was left stirring overnight. Precipitated N,N-dicyclohexylurea was filtered off and the filtrate evaporated under vacuum to give a crude residue diluted with acetonitrile; the second crop of N,N-dicyclohexylurea was filtered off and the filtrate, after evaporation of the solvent, was diluted with dichloromethane. The organic phase was washed with 2N HCl (2×10 mL), brine (15 mL), dried over Na$_2$SO$_4$, and evaporated under vacuum to give R(−)2-(4'-isobutyl)-phenylpropionyl-(2"-N-benzyloxycarbamoylamino)-ethanesulfonamide as white powder (0.44 g; 0.98 mmol).; m.p.=107–109° C.; TLC (CH$_2$Cl$_2$/CH$_3$OH 98:2) Rf=0.2; [α]$_D$=−47.4 (c=1; EtOH)

$^1$H- NMR (CDCl$_3$) δ ppm 7.45–7.30 (m, 5H); 7.25–7.05 (m, 5H, N$\underline{H}$); 5.4–5.3 (bs, 1H, N$\underline{H}$); 5.1 (s, 2H); 3.75–3.5 (m, 5H); 2.45 (d, 2H, J=7 Hz); 1.95–1.8 (m, 1H); 1.5 (d, 3H, J=7 Hz); 0.9 (d, 6H, J=7 Hz).

What is claimed is:

1. A method for inhibiting the chemotaxis and degranulation of neutrophils induced by interleukin 8 in a mammal, comprising the step of administering R(−)-2-[(4-Isobutyl)phenyl]propionamide to said mammal.

* * * * *